United States Patent
Ikadai et al.

(10) Patent No.: US 9,518,854 B2
(45) Date of Patent: Dec. 13, 2016

(54) RESONANCE CIRCUIT USED FOR MEASUREMENT DEVICE AND MEASUREMENT DEVICE

(71) Applicant: Yokogawa Electric Corporation, Musashino-shi, Tokyo (JP)

(72) Inventors: Yuki Ikadai, Musashino (JP); Masami Wada, Musashino (JP)

(73) Assignee: YOKOGAWA ELECTRIC CORPORATION, Tokyo (JP)

( * ) Notice: Subject to any disclaimer, the term of this patent is extended or adjusted under 35 U.S.C. 154(b) by 0 days.

(21) Appl. No.: 15/015,262

(22) Filed: Feb. 4, 2016

(65) Prior Publication Data
US 2016/0231156 A1   Aug. 11, 2016

(30) Foreign Application Priority Data
Feb. 5, 2015 (JP) ................. 2015-021146

(51) Int. Cl.
| | |
|---|---|
| *G01F 1/84* | (2006.01) |
| *G06G 7/16* | (2006.01) |
| *H03M 3/00* | (2006.01) |
| *H03K 5/02* | (2006.01) |

(52) U.S. Cl.
CPC ............ *G01F 1/8422* (2013.01); *G06G 7/16* (2013.01); *H03K 5/02* (2013.01); *H03M 3/30* (2013.01)

(58) Field of Classification Search
CPC ...................................... G01F 1/00; G01F 1/84
USPC ........................ 73/861.356; 702/45, 48
See application file for complete search history.

(56) References Cited

U.S. PATENT DOCUMENTS

| | | | | |
|---|---|---|---|---|
| 5,024,104 A | * | 6/1991 | Dames | .............. G01F 1/8413 73/861.357 |
| 6,227,059 B1 | * | 5/2001 | Schott | .............. G01F 1/8427 73/861.356 |
| 6,606,572 B2 | * | 8/2003 | Hansen | .............. G01F 1/8431 702/45 |

(Continued)

FOREIGN PATENT DOCUMENTS

| | | |
|---|---|---|
| JP | 2003-302272 A | 10/2003 |
| JP | 2012-88235 A | 5/2012 |

OTHER PUBLICATIONS

Communication dated Jun. 21, 2016, from the European Patent Office in counterpart European Application No. 16154304.6.

*Primary Examiner* — Jewel V Thompson
(74) *Attorney, Agent, or Firm* — Sughrue Mion, PLLC

(57) ABSTRACT

A resonance circuit is configured to receive a pulse density signal obtained by ΔΣ-modulating an analog displacement signal by a ΔΣ modulator and a multi-bit signal obtained from the pulse density signal and to generate an excitation signal based on the pulse density signal and the multi-bit signal. The resonance circuit includes an amplification factor controller configured to set an amplification factor depending on a vibration signal obtained from the multi-bit signal, a multiplier configured to amplify a level of the pulse density signal by the amplification factor, and a circuit group configured to generate the excitation signal based on a pulse density signal obtained by further ΔΣ-modulating an output of the multiplier. The amplification factor controller is configured to set the amplification factor using a proportional control and an integral control based a difference between an amplitude signal obtained from the vibration signal and a target amplitude value.

7 Claims, 9 Drawing Sheets

(56) References Cited

U.S. PATENT DOCUMENTS

| | | | |
|---|---|---|---|
| 8,776,614 B2* | 7/2014 | Wada | G01F 1/8436 341/143 |
| 2008/0041168 A1 | 2/2008 | Kolahi et al. | |
| 2011/0035166 A1 | 2/2011 | Henry et al. | |
| 2011/0166801 A1 | 7/2011 | Cunningham et al. | |

* cited by examiner

RESONANCE CIRCUIT USED FOR MEASUREMENT DEVICE AND MEASUREMENT DEVICE

CROSS-REFERENCE TO RELATED APPLICATION

The present application claims priority from Japanese Patent Application No. 2015-021146 filed on Feb. 5, 2015, the entire content of which is incorporated herein by reference.

BACKGROUND

Technical Field

The present invention relates to a resonance circuit used for a measurement device, which is configured to measure a physical quantity of a subject to be measured by vibrating an object, and the measurement device.

Related Art

As measurement devices, which are configured to measure a physical quantity of a subject to be measured by vibrating an object, such as the subject to be measured or a measurement piece, a Coriolis mass flowmeter is known. The Coriolis mass flowmeter is a measuring instrument using a Coriolis force acting when vertically vibrating a measurement tube, through which a fluid to be measured flows, with both ends thereof supported, and is configured to measure a mass flow rate of the fluid to be measured based on a phase difference between upstream and downstream sides of the measurement tube vibrating at a natural frequency thereof. The Coriolis mass flowmeter can also measure a density of the fluid to be measured flowing through the measurement tube by measuring a vibration frequency of the measurement tube.

As described in Patent Document 1, an amplitude of resonance is advantageously controlled depending on a diameter. However, if a circuit as described in Patent Document 1 is constructed with an analog circuit, the number of components, such as operational amplifiers, analog switches, calculating resistors and capacitors, constituting a filter, is increased, thereby causing a problem in that an area of a circuit board has to be increased and also the costs is increased. Contrarily, if distal signal processing is employed, an IC in which gate arrays, DSPs (Digital Signal Processors) and the like are integrated can be used, thereby reducing an area of the circuit board and lowering the costs.

In the Coriolis mass flowmeter requiring a high precision measurement, if a resonance circuit is constructed with a digital circuit, an AD convertor IC of a high precision $\Delta\Sigma$ type may be used when a digital signal to be inputted to the resonance circuit is generated.

In general, because the $\Delta\Sigma$-type AD convertor IC is equipped therein with a $\Delta\Sigma$ modulator and a digital low-pass filter (LPF), a delay is occurred when the LPF performs processing. Therefore, there is a problem in that a phase shift is caused when performing excitation by resonance, so that precision of vibration control is deteriorated and thus precision of measurement is also deteriorated.

In order to solve such a problem, Patent Document 2 discloses a Coriolis mass flowmeter having a high precision and stabilized resonance circuit, in which a delay is reduced while performing digital signal processing.

FIG. 9 is a block diagram showing a main configuration of the Coriolis flow mass meter described in Patent Document 2. A detector 510 has first and second sensor 512 and 514 for measuring displacements of upstream and downstream sides of a measurement tube (not shown), such as a U-shaped tube or a straight tube, through which a fluid to be measured flows, and a exciter 516 constituted of a driving coil and the like.

A pair of analog displacement signals outputted from the first sensor 512 and the second sensor 514 are respectively $\Delta\Sigma$-modulated by a first $\Delta\Sigma$ modulator 520 and a second $\Delta\Sigma$ modulator 522 and thus become 1-bit pulse density signals.

The pulse density signals are respectively converted to multi-bit signals (ordinary digital data) by a first LPF 524 and a second LPF 526. Two multi-bit signals are sent to the signal computing module 528 so that a mass flow rate and a density are calculated therefrom by a known technique.

The first $\Delta\Sigma$ modulator 520 and first LPF 524 and the second $\Delta\Sigma$ modulator 522 and second LPF 526 constitute, respectively, $\Delta\Sigma$-type AD convertors, and delays are occurred in the first LPF 524 and the second LPF 526.

An excitation circuit 530 is a circuit for driving the exciter 516 to excite the measurement tube. The excitation circuit 530 is operated by a pulse density signal outputted by the first $\Delta\Sigma$ modulator 520 and a multi-bit signal outputted by the first LPF 524.

The excitation circuit 530 includes a resonance circuit 532 for generating an excitation signal based on output signals of the sensors and a drive output module 534 for amplifying and returning the excitation signal to the exciter 516.

In the resonance circuit 532, a pulse height (level) of the pulse density signal outputted by the first $\Delta\Sigma$ modulator 520 is amplified by a multiplier 540. An amplification factor in the multiplier 540 is determined depending on an amplitude of the measurement tube. Namely, the smaller the amplitude of vibration than a target value, the higher the amplification factor is set. Also, if the amplitude comes close to the target value, the amplification is set to be close to 0.

Specifically, a first HPF 542 cuts a DC signal (offset signal) from the multi-bit signal outputted by the first LPF 124 to extract a vibration signal, which is an AC signal corresponding to vibration of the measurement tube. Then, an amplification factor controller 544 performs a proportional control based on the vibration signal and sets the amplification factor of the multiplier 540 so that the amplitude of the measurement tube is stabilized to a target value.

FIG. 10 is a block diagram showing a configuration of the amplification factor controller 544. The amplification factor controller 544 is configured so that an absolute valve of the AC signal outputted from the first HPF 542 and corresponding to vibration of the measurement tube is taken by an absolute circuit 560 performing rectification. Also, the fourth LPF 562 cuts a high frequency from the value, thereby smoothing the value. Therefore, an amplitude signal which is a DC signal corresponding to an amplitude of the measurement tube is obtained.

Also, a subtractor 564 calculates a difference value between the amplitude signal and a target amplitude value. The difference value is amplified by a variable amplifier 566 and then is set as an amplification factor for the multiplier 540.

Namely, a proportional control is performed in such a manner that if the amplitude signal is smaller than the target value, an output of the amplification factor controller 544 is increased and a gain of the resonance circuit 533 is increased, and on the other hand, if the amplitude signal comes close to the target value, the output of the amplification factor controller 544 comes close to 0 and the gain of the resonant 532 is decreased.

Meanwhile, a register 568 memorizes therein a cutoff frequency to be used in the fourth LPF 562, a target value to be used in the subtractor 564, an amplification factor (proportional gain) to be used in the variable amplifier 566. These values can be changed depending on a diameter of the measurement tube, thereby allowing a more stabilized control.

Returning to the description of FIG. 9, a multi-bit pulse density signal having a pulse height adjusted by the multiplier 540 is again ΔΣ-modulated by a third ΔΣ modulator 546 and thus becomes a 1-bit pulse density signal. If the pulse height is amplified by 1.2 times in the multiplier 540, the pulse density in the third ΔΣ modulator 546 becomes 1.2 times of itself, and also if the pulse height is amplified by 0.8 times in the multiplier 540, the pulse density in the third ΔΣ modulator 546 becomes 0.8 times of itself The pulse density signal outputted by the third ΔΣ modulator 546 is inputted to a DAC 548 and thus is converted to an analog signal. Then, the analog signal is inputted as an excitation signal to the drive output module 534 after a high frequency component (quantization noise) is removed therefrom by a third LPF 550 and also a DC signal is cut therefrom by a second HPF 552. The drive output module 534 amplifies the excitation signal to drive the exciter 516. Due to such a series of operations, excitation by resonance is performed.

As described above, in the Coriolis mass flowmeter described in Patent Document 2, the amplification factor of the pulse density signal outputted by the first ΔΣ modulator 520, in which a very small delay is occurred, is determined based on the output of the first LPF 524 in which a delay is occurred. Namely, the output of the first ΔΣ modulator 520 is used for a signal which is a reference for the excitation signal and in which a phase shift is not acceptable, and the output of the first LPF 524 is used for setting an amplification factor which is less influenced by a delay. Therefore, in the case of digital control, also, a high precision excitation by resonance having a reduced delay can be performed, thereby obtaining a stabilized amplitude.

Patent Document 1: Japanese Patent Application Publication No. 2003-302272

Patent Document 2: Japanese Patent Application Publication No. 2012-88235

As described above, in the based on-art Coriolis mass flowmeter, the amplification factor controller 544 for performing amplitude control sets an amplification factor for a signal to be returned to the exciter 516 using the proportional control.

However, setting of the amplification factor using the proportional control is likely to leave a steady-state deviation between an actual amplitude and a target value. On the other hand, if the amplification factor is increased to reduce the steady-state deviation, the control system is likely to be made unstable.

SUMMARY

Exemplary embodiments of the invention provide a resonance circuit used for a measurement device, in which a steady-state deviation between an actual amplitude and a target value is reduced without making a control system unstable, and the measurement device.

A resonance circuit used for a measurement device, according to an exemplary embodiment of the invention, is configured to receive a pulse density signal obtained by ΔΣ-modulating an analog displacement signal by a ΔΣ modulator and a multi-bit signal obtained from the pulse density signal and to generate an excitation signal based on the pulse density signal and the multi-bit signal. The resonance circuit comprises:

an amplification factor controller configured to set an amplification factor depending on a vibration signal obtained from the multi-bit signal;

a multiplier configured to amplify a level of the pulse density signal by the amplification factor; and a circuit group configured to generate the excitation signal based on a pulse density signal obtained by further ΔΣ-modulating an output of the multiplier;

wherein the amplification factor controller is configured to set the amplification factor using a proportional control and an integral control based a difference between an amplitude signal obtained from the vibration signal and a target amplitude value.

For the integral control, the amplification factor controller may have a limit value to an integrated value.

For the integral control, the amplification factor controller may be configured to set an integrated value to 0 if the amplitude signal exceeds a reference value.

The amplification factor controller may be configured so that if the integrated value is negative, the integrated value is limited to 0.

According to the present invention, a resonance circuit used for a measurement device can be provided, in which a steady-state deviation between an actual amplitude and a target value is reduced without making a control system unstable.

DETAILED DESCRIPTION

Figure 1:
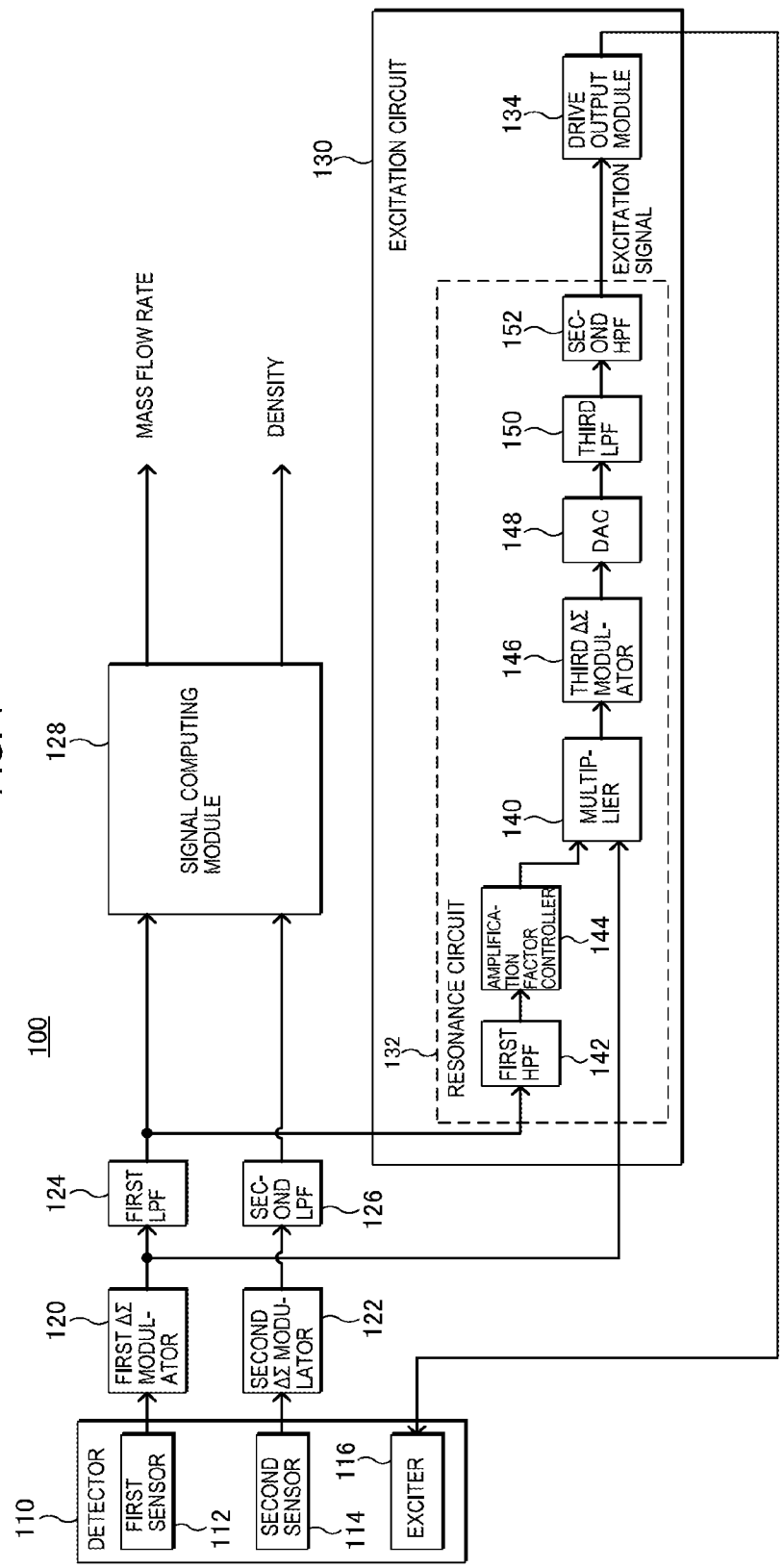
FIG. 1 is a block diagram showing a main configuration of a Coriolis mass flowmeter employing a resonance circuit according to the present embodiment.

Embodiments of the present invention will be described with reference to the accompanying drawings. FIG. 1 is a block diagram showing a main configuration of a Coriolis mass flowmeter 100 employing a resonance circuit 132 according to the present embodiment. Meanwhile, the resonance circuit of the present invention is not limited to the Coriolis mass flowmeter, but may be applied to any other measurement devices which are configured to measure a physical quantity by vibrating an object, such as a subject to be measured or a measurement piece.

As shown in this figure, the Coriolis mass flowmeter 100 has a detector 110, a first ΔΣ modulator 120, a second ΔΣ modulator 122, a first LPF 124, a second LPF 126, a signal computing module 128 and an excitation circuit 130.

The detector 110 has a first and second sensor 112 and 114 for measuring displacements of upstream and downstream sides of a measurement tube (not shown), such as a U-shaped tube or a straight tube, through which a fluid to be measured flows, and a exciter 116 constituted of a driving coil and the like.

A pair of analog displacement signals outputted from the first sensor 112 and the second sensor 114 are respectively ΔΣ-modulated by the first ΔΣ modulator 120 and the second ΔΣ modulator 122 and thus become 1-bit pulse density signals.

The pulse density signals are respectively converted to multi-bit signals (ordinary digital data) by the first LPF 124 and the second LPF 126. Two multi-bit signals are sent to the signal computing module 128 so that a mass flow rate and a density are calculated therefrom by a known technique.

The excitation circuit 130 is a circuit for driving the exciter 116 to excite the measurement tube. The excitation circuit 130 is operated by a pulse density signal outputted by the first ΔΣ modulator 120 and a multi-bit signal outputted by the first LPF 124.

The excitation circuit 130 includes a resonance circuit 132 for generating an excitation signal based on output signals of the sensors and a drive output module 134 for amplifying and returning the excitation signal to the exciter 116.

In the resonance circuit 132, a pulse height (level) of the pulse density signal outputted by the first ΔΣ modulator 120 is amplified by a multiplier 140. An amplification factor in the multiplier 140 is determined depending on an amplitude of the measurement tube.

Specifically, a first HPF 142 cuts a DC signal (offset signal) from the multi-bit signal outputted by the first LPF 124 to extract a vibration signal, which is an AC signal corresponding to vibration of the measurement tube. Then, an amplification factor controller 144 sets the amplification factor of the multiplier 140 based on the vibration signal, so that the amplitude of the measurement tube is stabilized to a target value. The detailed configurations and operations of the amplification factor controller 144 will be described below.

A multi-bit pulse density signal having a pulse height adjusted by the multiplier 140 is again ΔΣ-modulated by a third ΔΣ modulator 146 and thus becomes a 1-bit pulse density signal. The pulse density signal outputted by the third ΔΣ modulator 146 is inputted to a DAC 148 and thus is converted to an analog signal. Then, the analog signal is inputted as an excitation signal to the drive output module 134 after a high frequency component (quantization noise) is removed therefrom by a third LPF 150 and also a DC signal is cut therefrom by a second HPF 152. The drive output module 134 amplifies the excitation signal to drive the exciter 116. Due to such a series of operations, excitation by resonance is performed. Meanwhile, in the present example, the DAC 148, the third LPF 150 and the second HPF 152 are referred to as a circuit group for generating an excitation signal.

Figure 2:
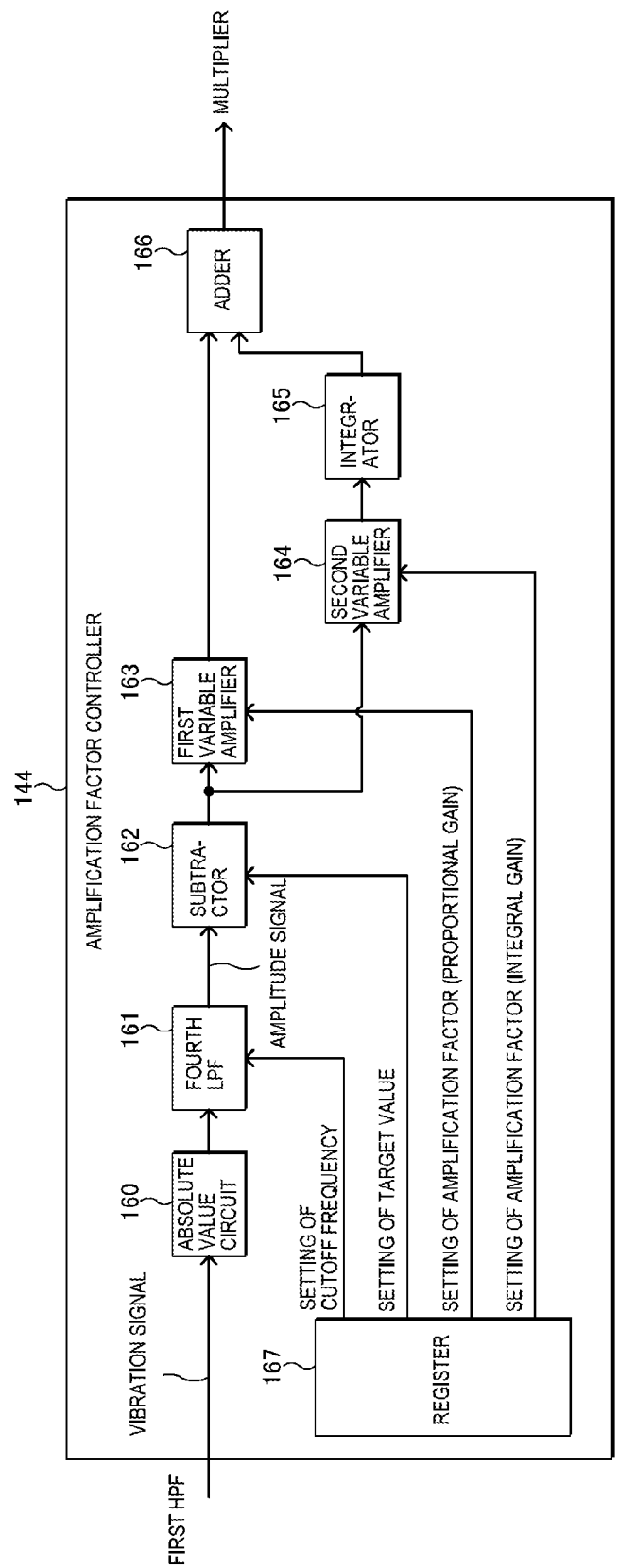
FIG. 2 is a block diagram showing a configuration of an amplification factor controller in the present embodiment.

FIG. 2 is a block diagram showing a configuration of the amplification factor controller 144 in the present embodiment. As shown in this figure, the amplification factor controller 144 has an absolute value circuit 160, a fourth LPF 161, a subtractor 162, a first variable amplifier 163, a second variable amplifier 164, an integrator 165, an adder 166 and a register 167.

Due to this configuration, the amplification factor controller 144 is configured so that an absolute valve of the vibration signal outputted from the first HPF 142 is taken by the absolute circuit 160 performing rectification. Also, the fourth LPF 161 cuts a high frequency from the value, thereby smoothing the value. Therefore, an amplitude signal, which is a DC signal corresponding to an amplitude of the measurement tube, is obtained.

Also, the subtractor 162 takes a difference value between the amplitude signal and a target amplitude value. A proportional control is performed by amplifying the difference value by the first variable amplifier 163, and also an integral control is performed by integrating a value, which is obtained by amplifying the difference value by the second variable amplifier 164, by the integrator 165.

Figure 3:
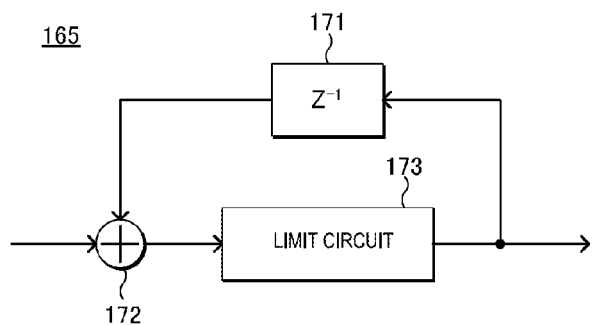
FIG. 3 is a block diagram showing a configuration example of an integrator 165.

FIG. 3 is a block diagram showing a configuration example of the integrator 165. An output integrated value passes through a time delay operator 171 and then is added to an input by the adder 172, thereby performing integration operation. An integral time constant τ can be defined, for example, as $\tau = Gp/Gi/fs$, where Gp is a proportional gain, Gi is an integral gain and fs is a sampling frequency in the amplification factor controller 144. In addition, the integrator 165 is provided with a limit circuit 173 to prevent the time delay operator 171 from being subject to overflow.

Returning to the description of FIG. 2, a value of the proportional control outputted by the first variable amplifier 163 and a value of the integral control outputted by the integrator 165 are added to each other in the adder 166 and then inputted to the multiplier 140 in the next stage.

The register 167 memorizes therein a cutoff frequency to be used in the fourth LPF 161, a target value to be used in the subtractor 162, an amplification factor (proportional gain) to be used in the first variable amplifier 163 and an amplification factor (integral gain) to be used in the second variable amplifier 164. These values can be changed depending on a diameter of the measurement tube, thereby allowing a more stabilized control. Meanwhile, it should be noted that when setting the proportional gain and the integral gain, stability of the control system, such as gain margin or phase margin, is taken into consideration to prevent oscillation or the like.

As described above, according to the present embodiment, the integral control of adding an integrated value of a deviation is performed in addition to the related-art proportional control, thereby reducing a steady-state deviation between an actual amplitude and a target value without making the control system unstable.

Figure 4:
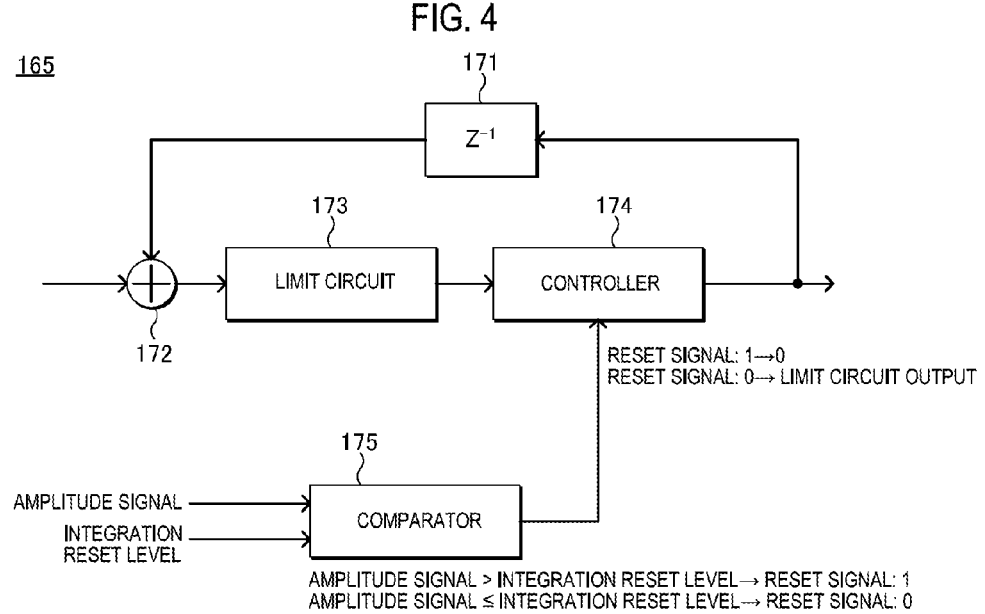
FIG. 4 is a block diagram showing the integrator having an integration reset function added thereto.

Alternatively, as shown in FIG. 4, an integration reset function realized by a controller 174 and a comparator 175 may be added to the integrator 165. In the example of this figure, an amplitude signal outputted by the fourth LPF 161 and a preset integration reset level (reference value) are compared to each other by the comparator 175. If the amplitude signal is equal to or higher than the integration reset level, the comparator 175 inputs a reset signal to the controller 174.

The controller 174 outputs 0 if the reset signal is inputted thereto, but otherwise outputs an output of the limit circuit 173 as it is. Accordingly, when the amplitude signal is equal to or higher than the integration reset level, the integrated value is reset.

For example, if air bubbles are entrained into a fluid to be measured, there is a case where an amplitude of the measurement tube is decreased and an output of the integrator 165 reaches a limit. At this state, if entrainment of air bubbles is stabilized, the integrator 165 attempts to bring the amplitude value close to the target value while the output thereof is the limit. Accordingly, there is a risk that an excessive integration is caused and the amplitude signal is continuously increased so that the detector 110 is abnormally vibrated.

Thus, if the amplitude signal outputted by the fourth LPF 161 exceeds the integration reset level, the integrated value is reset to prevent the excessive integration.

Figure 5:
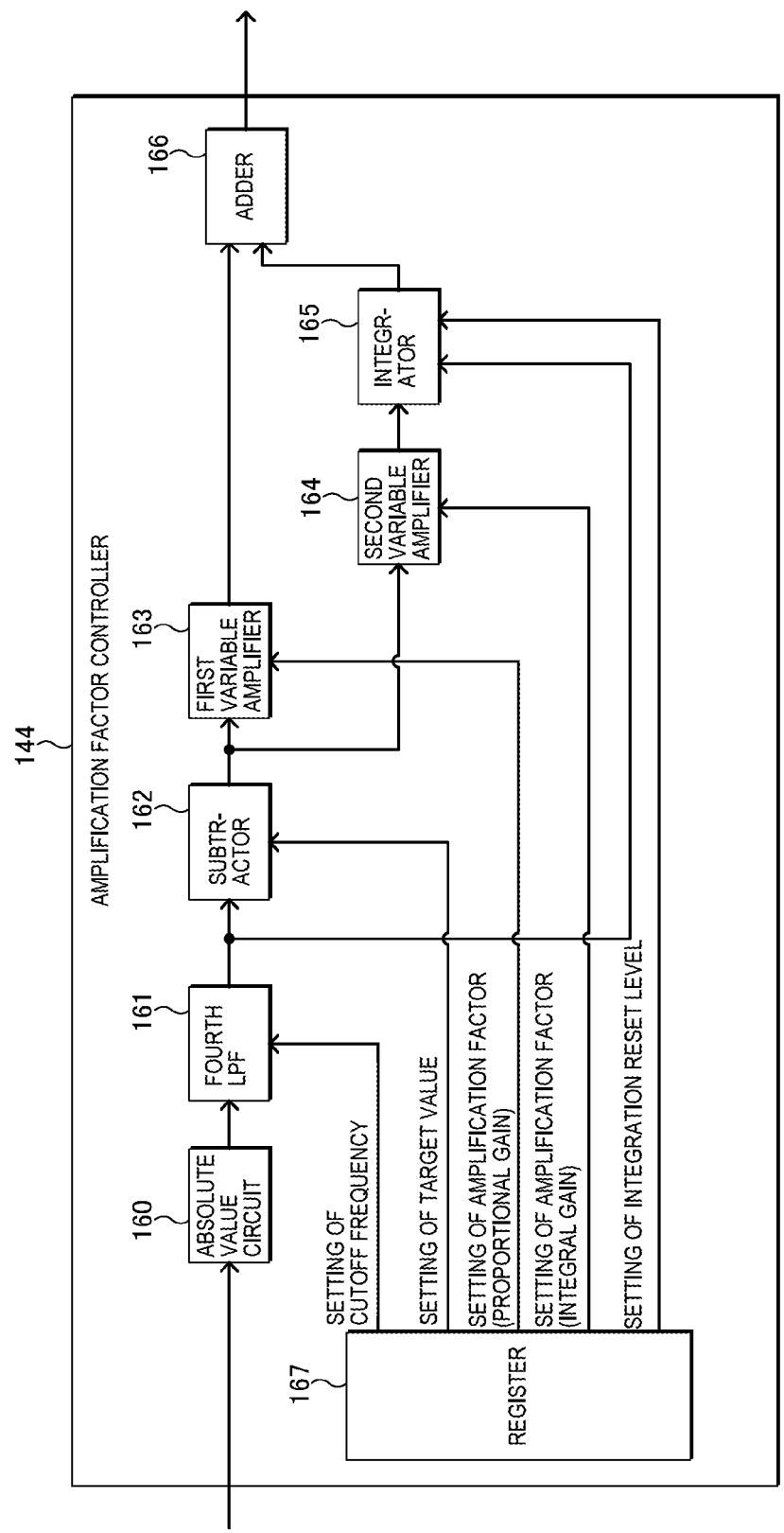
FIG. 5 is a block diagram showing a configuration of the amplification factor controller in a case where the integration reset function is added thereto.

Alternatively, in this case, the amplification factor controller 144 may be configured as shown in FIG. 5. Namely, the integration reset level may be previously set in the register 167, and the integration reset level and the output of the fourth LPF 161 may be inputted to the integrator 165 configured as shown in FIG. 4.

Figure 6:
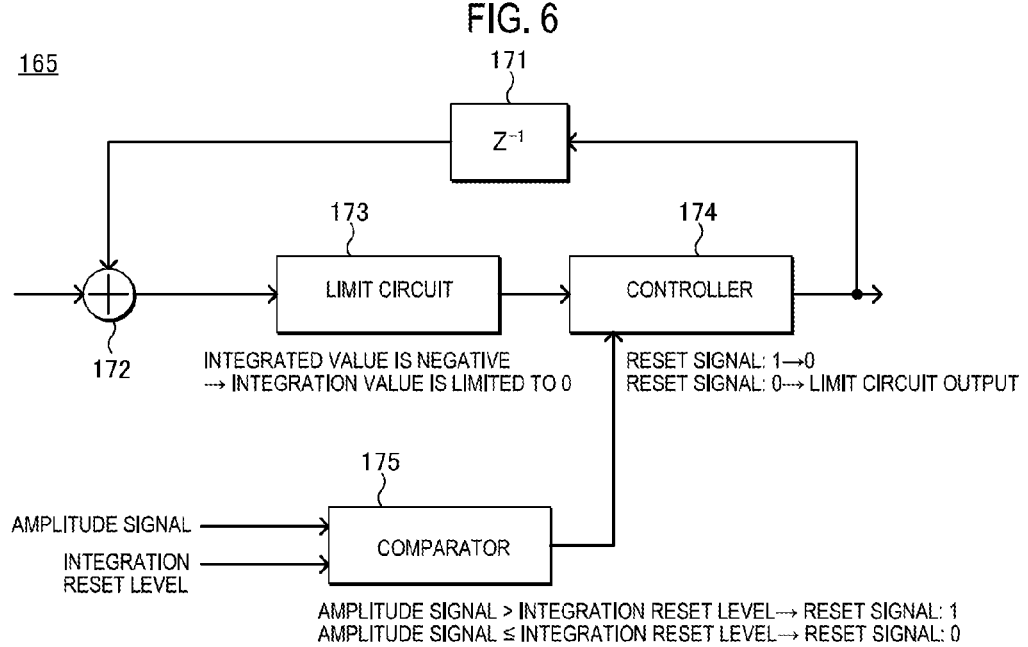
FIG. 6 is a block diagram showing a configuration of the amplification factor controller configured to limit an integrated value to 0 when the value is negative.

In addition, as shown in FIG. 6, the limit circuit 173 may limit the integrated value to 0 when the integrated value is negative. In this case, because during a period of 'the amplitude target value<the amplitude signal' after resetting, a negative integral cannot be performed, the integrated value can be smoothly returned to the target amplitude value.

Figure 7:
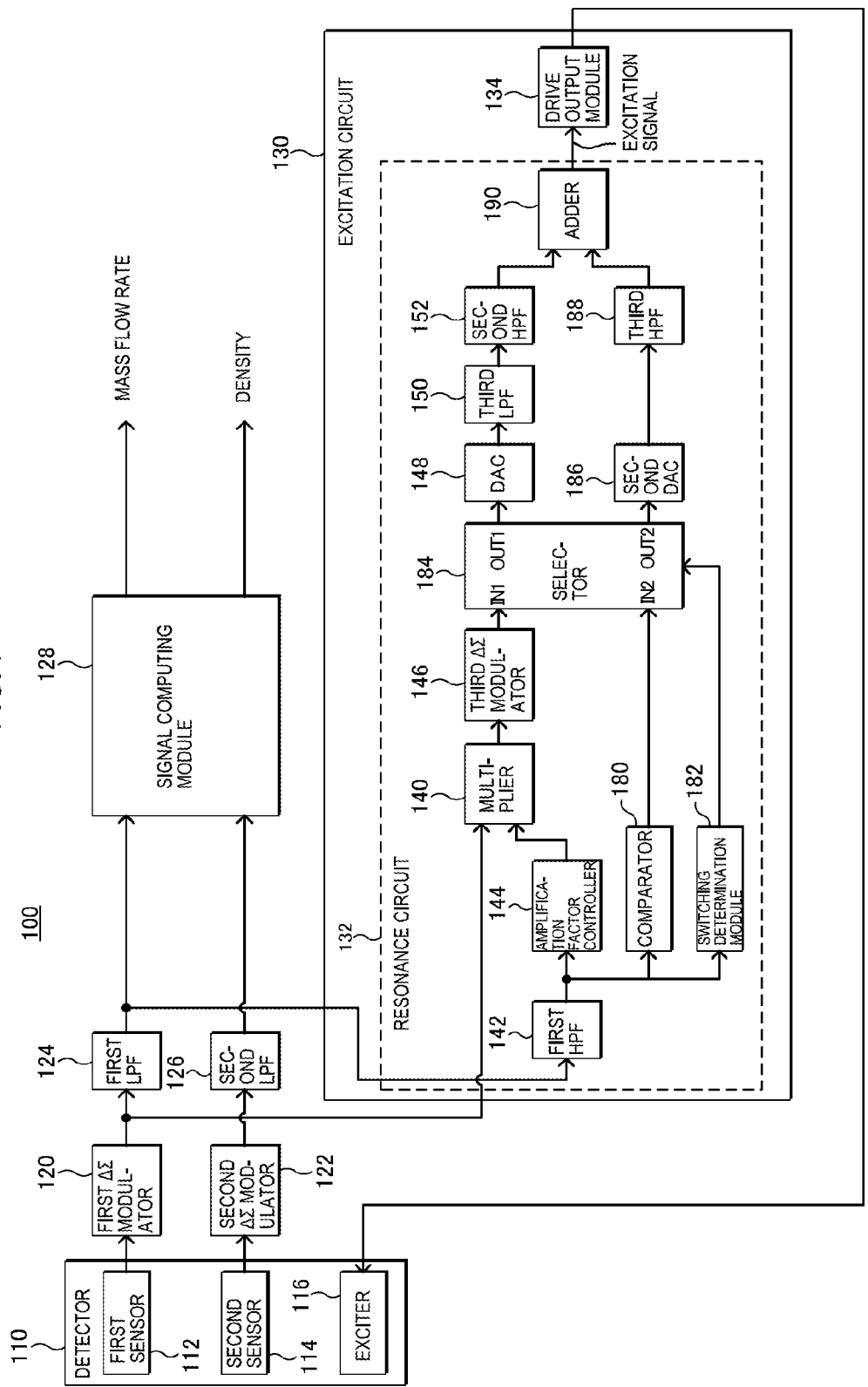
FIG. 7 is a block diagram showing an alternative example of a main configuration of a Coriolis mass flowmeter employing a resonance circuit according to the present embodiment.

FIG. 7 is a block diagram showing an alternative example of the main configuration of the Coriolis mass flowmeter 100 employing the resonance circuit 132 according to the present embodiment. The resonance circuit 132 of the alternative example is provided with a steady-state path and a startup-state path, which are switched between each other by a selector 184 so that either one thereof can be selectively used. In the steady-state path, an excitation signal of which amplitude is stabilized to a target value is generated, whereas in the startup-state path, an excitation signal of which amplitude rapidly reaches the target value is generated.

Before an excitation signal is outputted from the steady-state path and startup-state path to the drive output module 134, outputs of two paths are to be added by an adder 190, but signals of both paths are not added because only a signal of one path selected by the selector 184 is inputted to the adder 190.

In the steady-state path, a pulse height (level) of a pulse density signal outputted by a first ΔΣ modulator 120 is amplified by a multiplier 140. As described above, an amplification factor in the multiplier 140 is set by an amplification factor controller 144 using a proportional control and an integral control depending on an amplitude of the measurement tube.

A multi-bit pulse density signal having a pulse height adjusted by the multiplier 140 is again ΔΣ-modulated by a third ΔΣ modulator 146 and thus becomes a 1-bit pulse density signal. The pulse density signal outputted by the third ΔΣ modulator 146 is inputted to a DAC 148 through a path of IN1-OUT1 in the selector 184 and thus is converted to an analog signal. Then, the analog signal is inputted as an excitation signal to the drive output module 134 through the adder 190 after a high frequency component (quantization noise) is removed therefrom by a third LPF 150 and also a DC signal is cut therefrom by a second HPF 152. The drive output module 134 amplifies the excitation signal to drive an exciter 116. Due to such a series of operations, excitation by resonance during the steady state is performed.

In the startup-state path, a vibration signal outputted by a first HPF 142 is binarized using a comparator 180. Namely, if a displacement of the vibration is positive, H is outputted, whereas if a displacement of the vibration is negative, L is outputted.

An output of the comparator 180 is inputted to a second DAC 186 through a path of IN2-OUT2 in the selector 184 and thus is converted to a rectangular analog signal. Then, the analog signal is inputted as an excitation signal to the drive output module 134 through the adder 190 after a DC signal is cut therefrom by a third HPF 188. Accordingly, the excitation signal becomes a positive maximum value if a displacement of the vibration is positive, and becomes a negative maximum value if a displacement of the vibration is negative.

Namely, in the steady-state path, the amplification factor is set to correspond to an amplitude of the vibration and thus to obtain a constant amplitude, and in the startup-state path, maximum values corresponding to positive and negative displacements of the vibration are returned so that the amplitude can rapidly reach the target value.

Herein, switching of the selector 184 is controlled by a switching determination module 182. The switching determination module 182 generates an amplitude signal having a magnitude corresponding to an amplitude of the vibration signal outputted by the first HPF 142. Also, if the amplitude signal is smaller than a predetermined reference value, this case is considered as the startup state and thus the selector 184 is switched to the startup-state path, i.e., the path of IN2-OUT2. On the other hand, if the amplitude signal is larger than the predetermined reference value, this case is considered as the steady state and thus the selector 184 is switched to the steady-state path, i.e., the path of IN1-OUT1.

According to the present alternative example, likewise, the integral control of adding an integrated value of a deviation is performed in addition to the related-art proportional control, thereby reducing a steady-state deviation between an actual amplitude and a target value without making the control system unstable.

Figure 8:
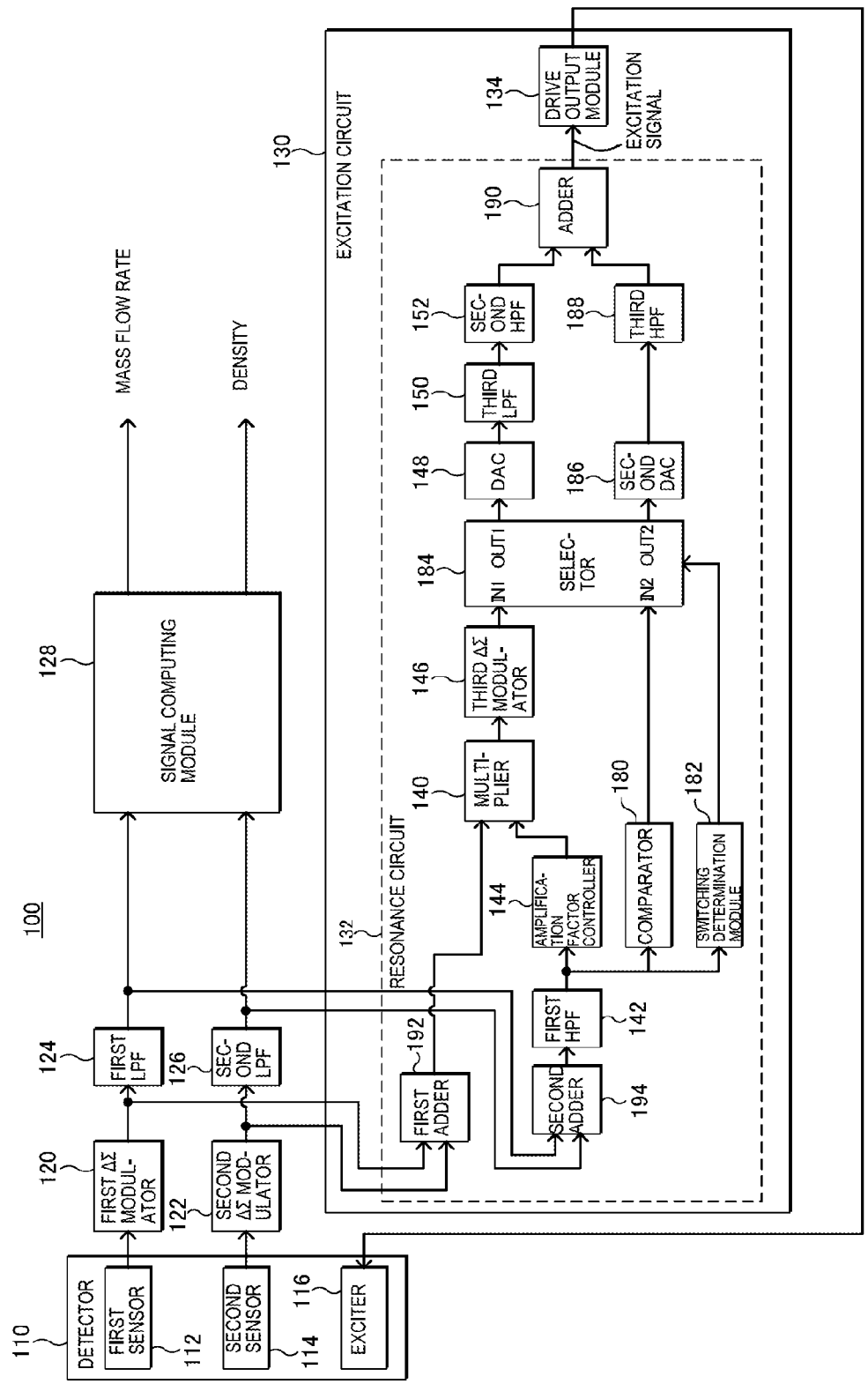
FIG. 8 is a block diagram showing a second alternative example of a main configuration of a Coriolis mass flowmeter employing a resonance circuit according to the present embodiment.
Figure 9:
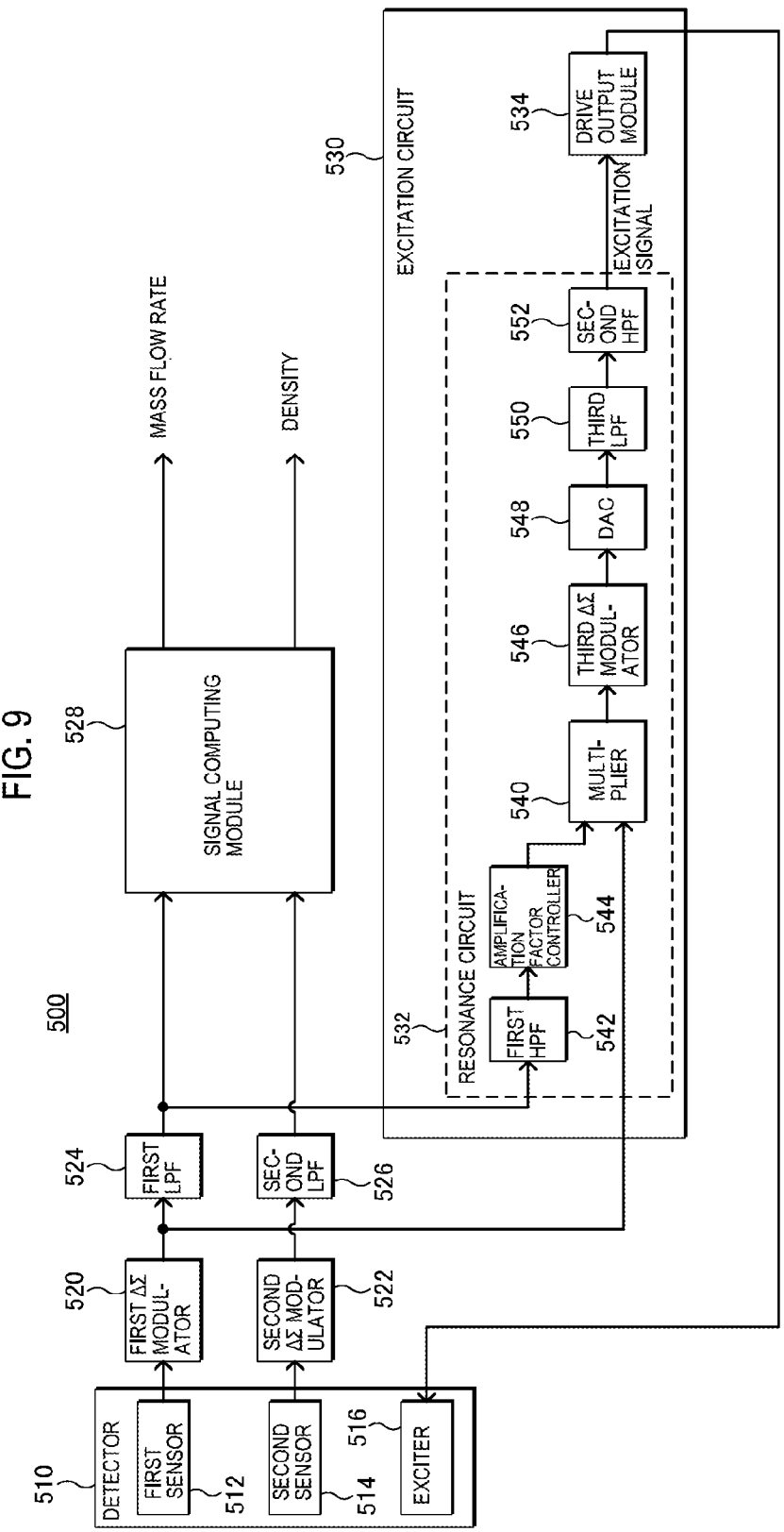
FIG. 9 is a block diagram showing a main configuration of a Coriolis mass flowmeter described in Patent Document 2.
Figure 10:
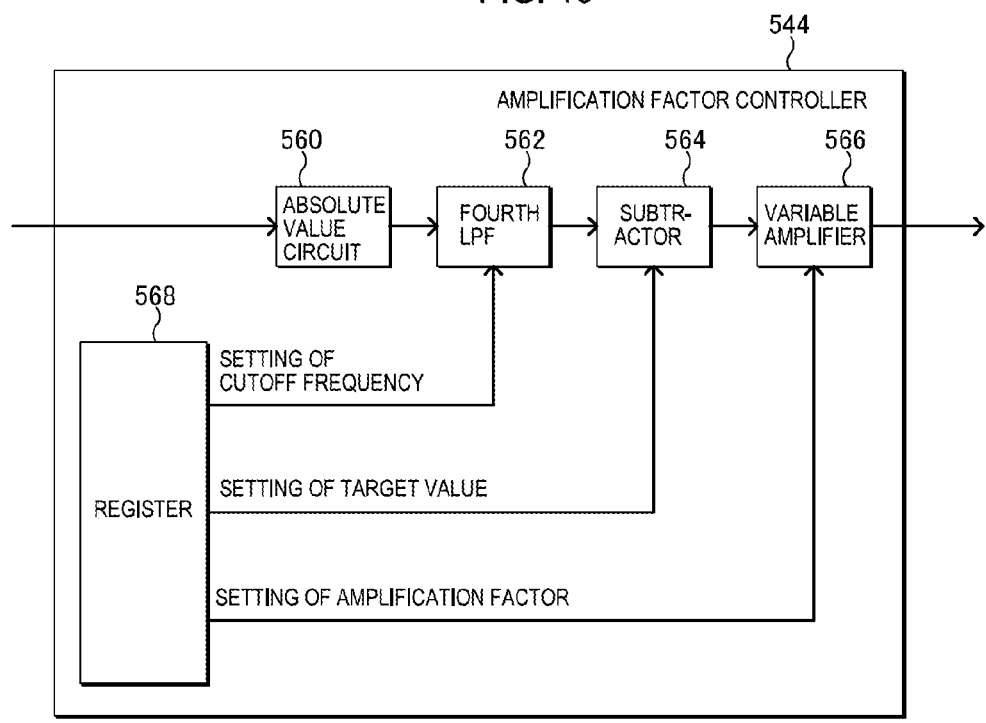
FIG. 10 is a block diagram showing a configuration of an amplification factor controller.

FIG. 8 is a block diagram showing a second alternative example of the main configuration of the Coriolis mass flowmeter 100 employing the resonance circuit 132 according to the present embodiment. In the foregoing alternative example, the output of the first ΔΣ modulator 120 is inputted to the multiplier 140 and the output of the first LPF 124 is inputted to the first HPF 142. However, according to the second alternative example, an output of a first ΔΣ modulator 120 and an output of a second ΔΣ modulator 122 are added in a first adder 192 and then inputted to a multiplier 140, and an output of a first LPF 124 and an output of a second LPF 126 are added in a second adder 194 and then inputted to a first HPF 142.

According to the second alternative example, even if an output of a first sensor 112 or an output of a second sensor 114 are temporarily disordered due to entrainment of air bubbles or the like, two outputs can be averaged to reduce an effect of the disorder.

Also, according to the second alternative example, likewise, the integral control of adding an integrated value of a deviation is performed in addition to the related-art proportional control, thereby reducing a steady-state deviation between an actual amplitude and a target value without making the control system unstable.

What is claimed is:

1. A resonance circuit used for a measurement device, configured to receive a pulse density signal obtained by ΔΣ-modulating an analog displacement signal by a ΔΣ modulator and a multi-bit signal obtained from the pulse density signal and to generate an excitation signal based on the pulse density signal and the multi-bit signal, the resonance circuit comprising:

- an amplification factor controller configured to set an amplification factor depending on a vibration signal obtained from the multi-bit signal;
- a multiplier configured to amplify a level of the pulse density signal by the amplification factor; and
- a circuit group configured to generate the excitation signal based on a pulse density signal obtained by further $\Delta\Sigma$-modulating an output of the multiplier;
- wherein the amplification factor controller is configured to set the amplification factor using a proportional control and an integral control based a difference between an amplitude signal obtained from the vibration signal and a target amplitude value.

2. The resonance circuit according to claim 1, wherein for the integral control, the amplification factor controller has a limit value to an integrated value.

3. The resonance circuit according to claim 1, wherein for the integral control, the amplification factor controller is configured to set an integrated value to 0 if the amplitude signal exceeds a reference value.

4. The resonance circuit according to claim 2, wherein the amplification factor controller is configured so that if the integrated value is negative, the integrated value is limited to 0.

5. The resonance circuit according to claim 1, wherein the amplification factor controller comprises an amplifier and an integrator, the amplifier configured to amplify the difference between the amplitude signal obtained from the vibration signal and the target amplitude value, the integrator configured to integrate a value outputted from the amplifier.

6. The resonance circuit according to claim 5, wherein the amplification factor controller further comprises another amplifier and an adder, the another amplifier configured to amplify the difference between the amplitude signal obtained from the vibration signal and the target amplitude value, the adder configured to add a value of the proportional control outputted by the another amplifier and a value of the integral control outputted by the integrator.

7. A measurement device comprising:

- a detector configured to output an analog displacement signal based on displacement of an object occurred when the object is vibrated;
- a $\Delta\Sigma$ modulator configured to $\Delta\Sigma$-modulate the analog displacement signal to output a pulse density signal;
- a low-pass filter configured to convert the pulse density signal to a multi-bit signal; and
- a resonance circuit configured to generate an excitation signal based on the pulse density signal and the multi-bit signal, the resonance circuit comprising:
  - an amplification factor controller configured to set an amplification factor depending on a vibration signal obtained from the multi-bit signal;
  - a multiplier configured to amplify a level of the pulse density signal by the amplification factor; and
  - a circuit group configured to generate the excitation signal based on a pulse density signal obtained by further $\Delta\Sigma$-modulating an output of the multiplier;
- wherein the amplification factor controller is configured to set the amplification factor using a proportional control and an integral control based a difference between an amplitude signal obtained from the vibration signal and a target amplitude value.

* * * * *